（12）United States Patent
Padiy

(10) Patent No.: US 9,587,991 B2
(45) Date of Patent: Mar. 7, 2017

(54) SUBSTRATE LAYER ADAPTED TO CARRY SENSORS, ACTUATORS OR ELECTRICAL COMPONENTS

(75) Inventor: Alexander Padiy, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1426 days.

(21) Appl. No.: 12/992,321

(22) PCT Filed: May 18, 2009

(86) PCT No.: PCT/IB2009/052044
§ 371 (c)(1),
(2), (4) Date: Nov. 12, 2010

(87) PCT Pub. No.: WO2009/141780
PCT Pub. Date: Nov. 26, 2009

(65) Prior Publication Data
US 2011/0069459 A1   Mar. 24, 2011

(30) Foreign Application Priority Data

May 23, 2008   (EP) .................................. 08156802

(51) Int. Cl.
| H05K 1/00 | (2006.01) |
| H05K 1/18 | (2006.01) |
| H05K 7/00 | (2006.01) |
| G01K 1/16 | (2006.01) |
| A61B 5/01 | (2006.01) |
| G01K 13/00 | (2006.01) |
| A61B 5/00 | (2006.01) |

(52) U.S. Cl.
CPC ................ *G01K 1/165* (2013.01); *A61B 5/01* (2013.01); *G01K 13/002* (2013.01); *A61B 5/68* (2013.01); *A61B 2562/0271* (2013.01); *A61B 2562/0276* (2013.01); *A61B 2562/164* (2013.01); *Y10T 29/4913* (2015.01); *Y10T 428/24314* (2015.01)

(58) Field of Classification Search
USPC ........................................ 361/748, 760, 761
See application file for complete search history.

(56) References Cited

U.S. PATENT DOCUMENTS

| 5,746,207 A * | 5/1998 | McLaughlin et al. ......... 600/372 |
| 6,385,473 B1 * | 5/2002 | Haines et al. ................. 600/393 |
| 6,454,725 B1 | 9/2002 | Yu |
| 6,964,205 B2 * | 11/2005 | Papakostas ............... G01L 1/20 73/862.046 |

(Continued)

FOREIGN PATENT DOCUMENTS

| DE | 29907768 U1 | 12/1999 |
| GB | 2276326 A | 9/1994 |

(Continued)

*Primary Examiner* — Andargie M Aychillhum

(57) ABSTRACT

A substrate layer structure (100) is adapted to carry electronic device, or components, or electro-mechanical, or electro-chemical sensors, or a combination thereof, and is adapted to be attached to a surface of a human or animal body or biological species. The surface of the flexible substrate layer structure is patterned with a pre-fixed geometry formed by one or more slits (101-701, 502-702). The geometry is selected such that a stretchability of the substrate layer structure becomes adapted to the geometry of the body surface under it.

22 Claims, 3 Drawing Sheets

(56) References Cited

U.S. PATENT DOCUMENTS

| | | | |
|---|---|---|---|
| 7,619,168 B2 * | 11/2009 | Togashi | 174/260 |
| 7,625,117 B2 * | 12/2009 | Haslett et al. | 374/111 |
| 2002/0107435 A1 * | 8/2002 | Swetlik | A61B 5/0006 |
| | | | 600/382 |
| 2003/0006971 A1 | 1/2003 | Blanchard | |
| 2003/0069714 A1 | 4/2003 | Wigley et al. | |
| 2004/0030258 A1 | 2/2004 | Williams et al. | |
| 2004/0133092 A1 | 7/2004 | Kain | |
| 2004/0176672 A1 | 9/2004 | Silver et al. | |
| 2005/0034485 A1 | 2/2005 | Klefstad-Sillonville et al. | |
| 2005/0141591 A1 * | 6/2005 | Sakano | 374/163 |
| 2005/0226310 A1 | 10/2005 | Nakazawa et al. | |
| 2005/0257628 A1 * | 11/2005 | Nikaido et al. | 73/862.541 |
| 2006/0071349 A1 * | 4/2006 | Tokushige | H01L 23/5387 |
| | | | 257/784 |
| 2006/0238428 A1 | 10/2006 | Schmitt et al. | |
| 2007/0001796 A1 * | 1/2007 | Waffenschmidt et al. | 336/223 |
| 2007/0034818 A1 * | 2/2007 | Grummon | 251/129.01 |
| 2007/0167859 A1 | 7/2007 | Finneran et al. | |
| 2007/0285225 A1 * | 12/2007 | Koyama | A61B 5/0002 |
| | | | 340/539.12 |
| 2008/0000304 A1 | 1/2008 | Nagle et al. | |
| 2008/0154110 A1 | 6/2008 | Burnes et al. | |
| 2009/0270745 A1 * | 10/2009 | Sankai | A61B 5/6814 |
| | | | 600/504 |

FOREIGN PATENT DOCUMENTS

| | | |
|---|---|---|
| JP | 62020393 A | 1/1987 |
| JP | 6246857 A | 9/1994 |
| JP | H11-219623 | 8/1999 |
| JP | 2007209428 A | 8/2007 |

* cited by examiner

SUBSTRATE LAYER ADAPTED TO CARRY SENSORS, ACTUATORS OR ELECTRICAL COMPONENTS

FIELD OF THE INVENTION

The present invention substrate layer structure adapted to carry sensors, actuators or electronic components and adapted to be attached to a surface of a human or animal body or biological species.

BACKGROUND OF THE INVENTION

Many different medical applications require that patients carry medical sensors on a daily basis. An example of such medical sensors is body temperature sensors, which can either be based on invasive body temperature sensors (arterial line catheters, esophageal/rectal probes, etc.) or non-invasive sensors which are attached to the surface of the subject being monitored.

Experience shows that one of the most importance factors for the patients carrying such non-invasive medical sensors is that they are flexible & stretchable as needed for both high-quality reliable attachment to the body and for ensuring high measurement accuracy and reliability with respect to measurement artifacts. This is definitely the case in case of temperature sensors as they require well-defined stable thermal contact between the skin and the sensor for proper operation. Typically, sensor curvature radius of a few cm (exact curvature is dependent on patient-specific geometry of the sensor placement location) needs to be achievable in case of the temperature sensor that is normally placed on the forehead. Even smaller curvatures of sub-cm scale might be needed when the sensor has to be placed at other locations on the body. In most cases, medical sensors need to be placed either on an ellipsoid-like object or in an ellipsoid-like depression. Therefore, it is not sufficient for the sensors to be able to bend in one direction; they also need to be stretchable.

The use of industry standard manufacturing processes is essential for achieving high yield, high reliability and low manufacturing cost of products. That is especially important in the considered case of consumable medical sensors, where both low cost and high reliability have high priority. Unfortunately, neither standard printed circuit board (PCB) materials nor standard flex-foil materials (e.g. polyimide film) satisfy the requirement of stretchability: PCB substrates are rigid (i.e. neither stretchable nor flexible), and flex-foil substrates are flexible but not stretchable. That makes them ill-suited for the considered class of body-worn anatomically conformal sensors.

The use of alternative substrates (e.g. textiles or rubber sheets) can also be in principle considered, but the corresponding manufacturing processed cannot yet compete with the PCB and flex-foil processed in terms of yield, product reliability and cost. Therefore, it is very much preferred to use the industry-standard PCB or flex-foil (e.g. polyimide) substrates.

BRIEF DESCRIPTION OF THE INVENTION

The object of the present invention is to overcome the above mentioned drawbacks by providing a flexible & stretchable substrate layer that is suitable to carry various electronic devices and thus forming flexible & stretchable medical device/sensor assembly, while at the same time making use of the proven industry-standard substrate materials and manufacturing processes.

According to one aspect the present invention relates to substrate layer structure adapted to carry sensors, actuators or electronic components, or a combination thereof, and adapted to be attached to a surface of a human or animal body or biological species, wherein the surface of the flexible substrate layer structure is patterned structure of pre-fixed geometry formed by one or more slits, the geometry being selected such that the stretchability of the substrate layer structure becomes adapted to the geometry of the body surface under it.

The geometry formed by the one or more slits can therefore be adapted to the usage condition of the substrate layer structure. Thus, if e.g. the implementation required that the stretchability is only one dimensional, the geometry may be made of multiple of parallel slits, if the geometry required is two dimensional in the plane of the layer structure, the geometry may be a formed by parallel S-shaped slits, and if the implementation requires that the stretchability is three dimensional a single slit that forms a spiral may be used. Accordingly, a highly advanced "stretchable electronic" circuit/sensor is provided.

In one embodiment, the substrate layer structure is made of an industry-standard printed circuit (PCB) board material.

The advantage of using the industry-standard substrates for mounting the electronic components is that it is possible to achieve high production throughput and high product reliability while simultaneously keeping the manufacturing costs low. An example of such PCB material is polyimide film, FR-2 (Phenolic cotton paper), FR-3 (Cotton paper and epoxy), FR-4 (Woven glass and epoxy), FR-5 (Woven glass and epoxy), FR-6 (Matte glass and polyester), G-10 (Woven glass and epoxy), CEM-1 (Cotton paper and epoxy), CEM-2 (Cotton paper and epoxy), CEM-3 (Woven glass and epoxy), CEM-4 (Woven glass and epoxy), CEM-5 (Woven glass and polyester), teflon, ceramic material.

In one embodiment, the one or more slits and thus the patterned structure of pre-fixed geometry is formed by cutting the slits into the surface of the substrate layer structure.

Thus, the desired level of stretchability and flexibility is achieved by forming slits in the substrate, for example, a spiral-shaped slit can be used to let the substrate stretch in the out-of-plane direction, e.g. in order to fit onto an elliptical or a conical object. Also, the so-called 'nested' slits can be exploited as to split the substrate layer structure into a number of sub-planes that allows e.g. pulling one of the spirals to the top while pulling the other spiral to the bottom. An object can be then placed in between the spirals. For example, a finger or an arm can be placed in between the spirals if the sensing principle requires the electronic components to be beneficially placed from both sides of the object being measured (e.g. a finger or an arm). Alternatively, 'nested' slits like 'dual-spiral' can be used for creating 'sandwich-like' multi-plane substrates wherein different planes are separated from each other by a certain material. In the case of the core body temperature sensor, a well-defined thermally insulating layer can be included in between the 'sandwich planes' in order to allow thermal flux measurement on the out-of-plane direction. The flexibility of the overall system is maintained if the insulation layer is chosen to be flexible and stretchable as well. It should be noted that the same 'sandwich' could be also achieved by using a number of separate substrates.

In one embodiment, the substrate layer structure is a sandwiched like structure formed by two or more of the PCB patterned structures.

Accordingly, a multilayer structures are obtained, which is often required for medical sensors such as temperature sensor, e.g. a temperature sensor so-called zero flux type that includes two or more temperature sensitive elements separated by a single layer (or more) of thermal insulation. Also, the each of the PCB patterned structures may be fit into another device. Depending on the application, the multilayer structures may be separated by an insulating material, e.g. in case the substrate layer structure is adapted to be used as a temperature sensor, or by non-insulating (or semi-conducting) material In one embodiment, the patterned structure of pre-fixed geometry is formed by:
  one or more substantially parallel straight lined slits, or
  one or more substantially parallel S-shaped slits, or
  a spiral shaped slit, or
  a dual spiral shaped slit, or
  a multi-spiral shaped slit, or
  a slit forming a cam-like structure, or
  a combination of two or more spiral shaped slits,
  a combination of a at least one S-shaped slit and at least one slit forming cam-like structure,
  a combination of two or more of the above.

Accordingly, the orientation of the stretchability may be fully controlled by varying the geometry of the slit(s). As mentioned previously, parallel slits as an example provide increased stretchability in one direction; S-shaped slits provide stretchability in two dimensions as well as the spiral shaped slit etc.

In one embodiment, the electronic device is electrical components, or circuitry, or both.

According to another aspect, the present invention relates to a method of manufacturing the substrate layer structure includes:
  providing said substrate layer structure,
  forming said one or more slits of pre-fixed geometry into the surface of the substrate layer structure, and
  placing or attaching said sensors, actuators, electronic components, or a combination thereof to the substrate layer structure.

It should be noted that the cut/slits may be performed right before or after placing the said electronic device or components, or electro-mechanical, or electro-chemical sensors. Making the slits as such is a standard and well known procedure as 'carving out' of the individual devices from the common substrate sheet (typical device size is in the order of a few cm, while the substrates are normally some 30 cm by 60 cm in size—depending on the manufacturing equipment and manufacturer preferences).

According to still another aspect, the present invention relates to a sensor assembly comprising said substrate layer structure and electronic device or components, or electro-mechanical, or electro-chemical sensors, or a combination thereof attached or integrated into the substrate layer structure.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
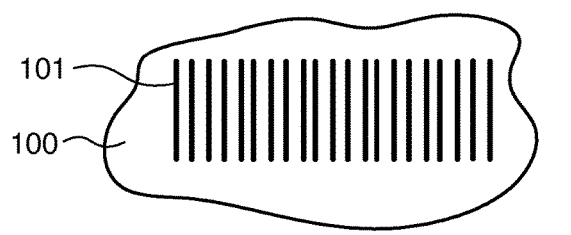
FIGS. 1-7 show seven different embodiment of substrates layer structure adapted to carry electronic device and adapted to be attached to a surface of a human or animal body or biological species.
Figure 1:
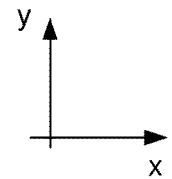

The use of industry standard manufacturing processes is important for achieving high yield, high reliability and low manufacturing cost of products. That is especially important in the considered case of consumable medical sensors, where both low cost and high reliability have high priority.

When a device includes a multiplicity of interconnected electrical components, rigid printed circuit boards (PCBs) or flexible foils used as substrate (flex-foils) are widely used in manufacturing to hold the components and to provide the required electrical interconnect between them. Such conducting layers are typically made of thin copper foil. Often, PCB factories use prepregs (short for preimpregnated), which are a combination of glass fiber mat, nonwoven material and resin. Copper foil and prepreg are typically laminated together with epoxy resin. Well known prepreg materials used in the PCB industry are FR-2 (Phenolic cotton paper), FR-3 (Cotton paper and epoxy), FR-4 (Woven glass and epoxy), FR-5 (Woven glass and epoxy), FR-6 (Matte glass and polyester), G-10 (Woven glass and epoxy), CEM-1 (Cotton paper and epoxy), CEM-2 (Cotton paper and epoxy), CEM-3 (Woven glass and epoxy), CEM-4 (Woven glass and epoxy), CEM-5 (Woven glass and polyester). Other widely used materials are polyimide, teflon and some ceramics. The use of alternative substrates such as textiles or rubber sheets can also be in principle considered, but the corresponding manufacturing processed cannot yet compete with the PCB and flex-foil processed in terms of yield, product reliability and cost. Therefore, it is preferred to use PCB or flex-foil substrates.

As discussed previously, flexibility and stretchability are very important in case of physiological sensors that need good anatomical fit with the body surface for proper operation. This is definitely the case with temperature sensors. For example, sensor curvature radius of a few cm (exact curvature is patient-specific) needs to be achievable in case of the forehead temperature sensor. Even smaller curvatures of sub-cm scale might be needed when the sensor has to be placed at location on the body like in the pocket behind the ear, in the arm pit, in the nose cavity, in the ear, in between the fingers or toes, or any other desired location on the body.

It should be noted that in both cases described above, the sensors need to be placed either on an ellipsoid-like object or in an ellipsoid-like depression. Therefore, it is not sufficient for the sensors to be able to bend in one direction; they also need to be stretchable.

Unfortunately, neither standard PCB materials nor standard flex-foil materials (e.g. polyimide film) satisfy the requirement of stretchability: PCB substrates are rigid (i.e. neither stretchable nor flexible), and flex-foil substrates are flexible but not stretchable. That makes them ill-suited for the considered class of body-worn anatomically conformal sensors.

FIGS. 1-7 show seven different embodiment of substrates layer structure adapted to carry electronic device and adapted to be attached to a surface of a human or animal body or biological species. The surface of the flexible substrate layer structures comprises a patterned structure of pre-fixed geometry, which may be formed by one or more slits, or by cutting out a pre-fixed geometry forming thus a so-called pre-fixed "nested" geometry (e.g. a spiral), where the geometry is selected such that the stretchability of the substrate layer structure becomes adapted to the geometry of the body surface under it.

The slits may be produced by well known methods such as simply by cutting into the substrate layer, or via standard etching methods, or by any other means that are available to the person skilled in the art. Further, the stretchability by be further controlled by varying the depth of the slits, but the depth typically extends only partially into the substrate layers, but the depth may just as well extend throughout the substrates layer, depending on the applications.

FIG. 1 shows a substrate layer structure 100 where the patterned structure includes substantially straight lines which provides an improved flexibility in x-direction (see the coordinate system). As depicted, the slits are formed by etching/cutting the slits into the substrate layer structure which may be a rigid printed circuit board (PCB), or a flexible foil, or a deformable material. The electronic device or devices, e.g. temperature sensitive element, may then be attached, soldered, mounted, to the patterned structure, e.g. at the slits 101, or at the layer structure 100. In a particular embodiment, temperature-sensitive elements (e.g. thermistors) can be mounted in between the slits. Such a sensor can be useful for measuring a multitude of temperatures e.g. on a finger or an arm near or at a joint.

Figure 2:
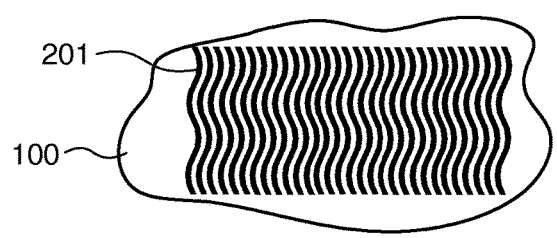
Figure 2:
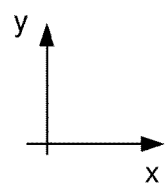

FIG. 2 shows a substrate layer structure 100 where the patterned structure includes substantially parallel S-shaped slits. Thus, in addition to the improved flexibility in x-direction a simultaneous flexibility in the y-direction is achieved, thus leading to improved "stretchability". Again, the electronic device or devices may be attached to the patterned structure, e.g. at the S-shaped slits 201, or at the layer structure 100.

Figure 3:
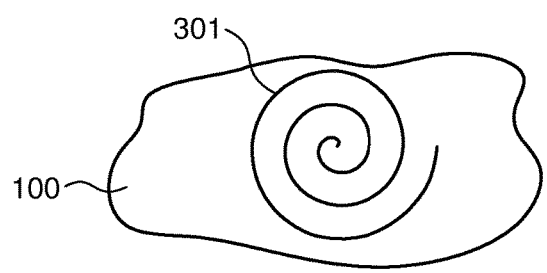
Figure 3:
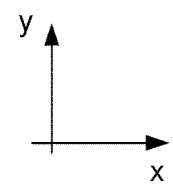

FIG. 3 shows a substrate layer structure 100 where the patterned structure includes a single slit 301 having spiral shape. Such a spiral cut causes high flexibility in both x-y-directions, especially the inner tip of the spiral. Additionally, such a spiral shaped structure provides significant stretchability in the z-direction (out-of-plane direction), e.g. in order to fit onto an elliptical or a conical object.

Figure 4:
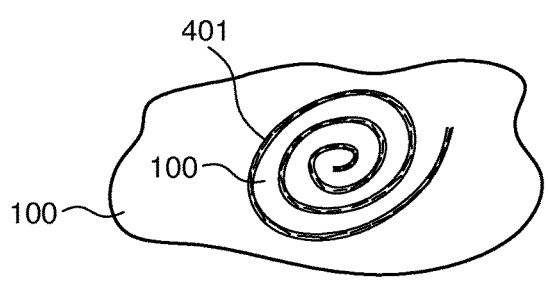
Figure 4:
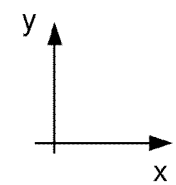

FIG. 4 shows a dual-spiral or "nested" slits 401 that are placed onto the substrate layer structure 100 and thus form a top layer 401. The use of such dual-spiral slit allows as an example an easy implementation of two layer sensor structures that are extremely flexible and self-aligned. Such a structure can be very useful in creating multi-layer structures, e.g. so-called zero heat flux type (or related) sensors (see FIG. 8) that include two or more temperature sensitive elements (thermistors, thermocouples, etc.) separated by a layer of thermal insulation, where the core body temperature is estimated by combining the multiplicity of the temperature readings. In particular, the difference between the temperatures on the opposite sides of the insulation layer (that is proportional to the heat flux from the measured body and the ambient) is being used in the estimation. In some embodiments the heat flux from the body to the ambient can be optionally modulated by the use of heating elements, evaporators, layers of variable effective thermal conductance and alike in order to increase the estimation accuracy. Thus, the use of "nested" slits allows low-cost manufacturing of multi-layer structures from a single substrate sheet and additionally simplifies the problem of aligning the different layers.

Figure 5:
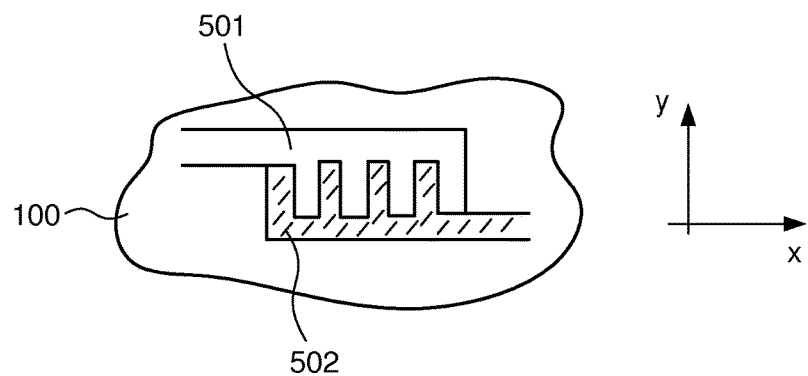
Figure 6:
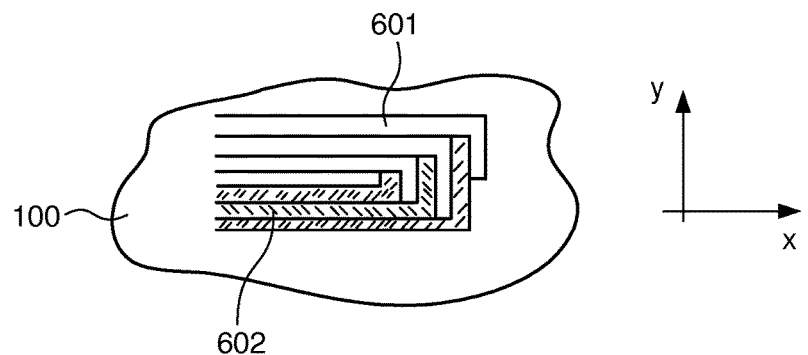
Figure 7:
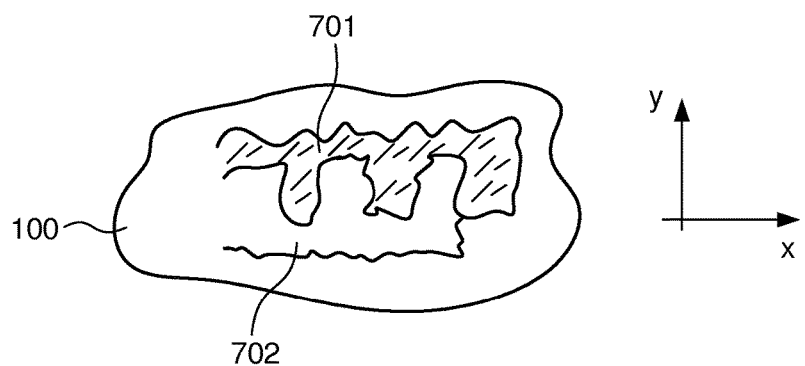

FIGS. 5-7 show three embodiments of slits forming cam-likes structures. In FIG. 5 the structures 501 and 502 have different depth into the substrate layer structure 100 and thus allow two-layer sensor structures that are flexible and stretchable in x-y-directions, i.e. the electronic device(s) can be placed into each respective structure 501, 502.

FIG. 6 shows a "nested" cam-like structure where the structures are put on that top of the substrate layer structure 100. FIG. 7 shows a combination of cam-like and S-shape slits 701, 702 such that additional flexibility and stretchability is achieved. By the term 'nested' is simply meant that it allows creating a multiplicity of 'sub-planes'.

Figure 8:
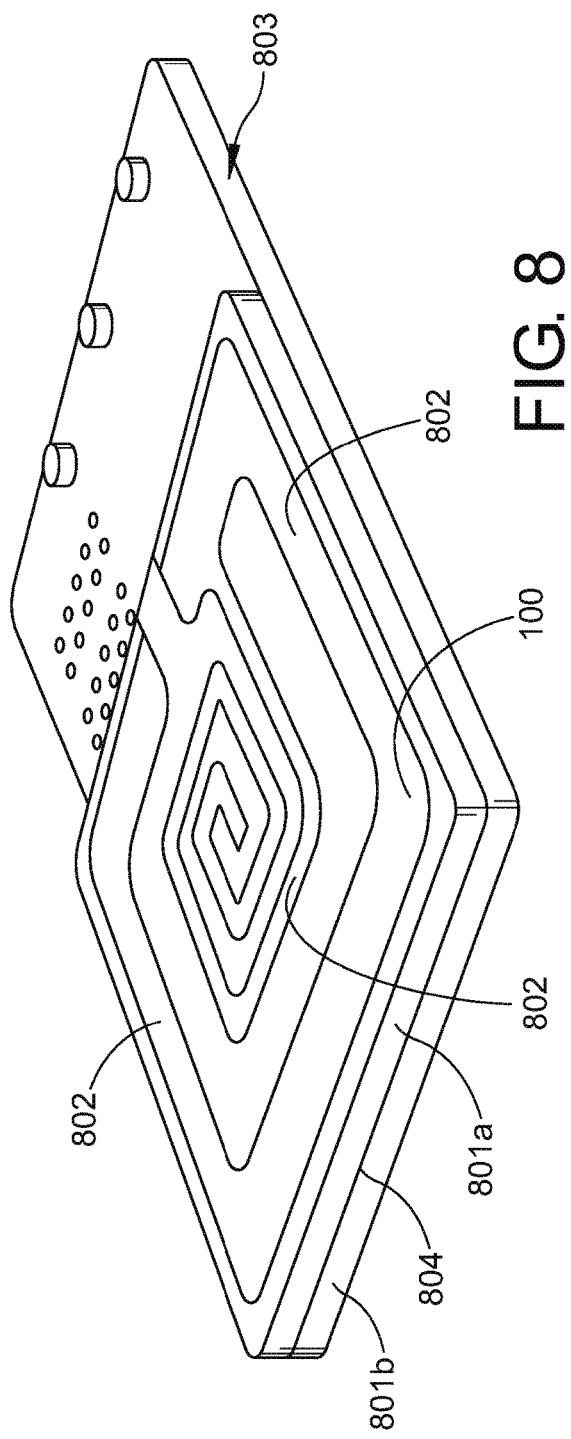
FIG. 8 shows one example of a temperature sensor assembly benefiting from using such substrates layer structure.

FIG. 8 shows one example of a flexible and stretchable sensor assembly that forms a temperature sensor. The substrate layer 100 is a "nested" spiral having attached thereto a number of temperature sensors (thermistors) 802. The other part of the spiral also contains thermistors 804 that is located between the insulation layer 801a and 801b (the dark separator between top 801b and bottom 801a). Both parts of the spiral are connected to few pieces of driving electronics 803.

It should be noted that any medical sensor containing electronic components would significantly benefit from using the slits as suggested for improving anatomical fit.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. A substrate layer structure configured to carry sensors, actuators, electronic components, or a combination thereof, and configured to be attached to a surface of a human or animal body or biological species, the layer structure including:
   a first flexible substrate layer which includes a pattern defined by one or more slits of pre-fixed geometry in the first flexible layer, and the geometry selected such that the first flexible substrate layer stretches to a geometry of the body surface adjacent the first flexible substrate layer; and
   wherein the pattern of the pre-fixed geometry of the first flexible substrate layer is formed by a slit forming a cam-like structure.

2. The substrate layer structure according to claim 1, wherein the first flexible substrate layer includes a printed circuit board (PCB) material.

3. The substrate layer structure according to claim 2, wherein the one or more slits in the first flexible layer define a nested spiral in the first flexible substrate layer.

4. The substrate layer structure according to claim 1, further including:
   a second flexible substrate layer sandwiched with the first flexible substrate layer, and the second flexible substrate layer includes one or more slits of the pre-fixed geometry cut or etched in a surface of the first flexible substrate layer.

5. The substrate layer structure according to claim 4, further including:
a second flexible substrate layer connected with the first flexible substrate layer, and the second flexible substrate layer includes one or more slits of the pre-fixed geometry in a surface of the pattern of the first flexible substrate layer, and the slits of the first and second substrate layers stretch to conform to the surface of the human or animal body or biological species between the layers.

6. The substrate layer structure according to claim 1, wherein the pattern of the pre-fixed geometry of the first flexible substrate layer is formed by at least one of:
substantially parallel S-shaped slits,
a spiral shaped slit,
a dual spiral shaped slit,
a multi-spiral shaped slit, or
a combination of two or more spiral shaped slits.

7. A sensor assembly comprising the substrate layer structure according to claim 1; and
sensors, actuators, electronic components, or a combination thereof attached or integrated into the first flexible substrate layer.

8. The sensor assembly according to claim 7, wherein the sensors include at least one temperature sensitive element.

9. The sensor assembly according to claim 8, further including:
two temperature sensitive elements separated by an insulating layer.

10. The sensor assembly according to claim 9, wherein the insulating layer includes:
a second flexible substrate layer sandwiched with the first substrate layer, the pattern being cut or etched into the first and second substrate layers.

11. The substrate layer structure according to claim 1, wherein the pattern of the pre-fixed geometry of the first flexible substrate layer is formed by at least one of:
a spiral shaped slit,
a dual spiral shaped slit,
a multi-spiral shaped slit, or
a combination of two or more spiral shaped slits.

12. The substrate layer structure according to claim 1, wherein the pattern of the pre-fixed geometry of the first flexible substrate layer is formed by a combination of two or more:
parallel slits extending transverse to a long axis of the first flexible substrate layer,
spiral slits, and
cam-like slits defined in a plane of the first flexible substrate layer to permit the flexible substrate layer to flex out of the plane.

13. The substrate layer structure according to claim 1, wherein the one or more slits have varying depths to control the stretchability of the first flexible substrate layer.

14. The substrate layer structure according to claim 1, further including:
a temperature sensitive element attached to or embedded in the first flexible substrate layer.

15. The substrate layer structure according to claim 1, wherein the first flexible substrate layer includes a flex-foil.

16. The substrate layer structure according to claim 1, wherein the slits are configured such that the first flexible substrate layer stretches and expands in three dimensions.

17. The substrate layer structure according to claim 1, wherein the first flexible substrate layer has a thickness in a z-direction and a surface which extends along an x and y direction, and wherein the slits are cut or etched in the z-direction into the surface with each slit extending in part in the x-direction and in part in the y-direction.

18. The substrate layer structure according to claim 1, wherein the slit forming the cam-like structure has a different depth into the first flexible substrate layer than a second slit forming a second cam-like structure.

19. The substrate layer structure according to claim 1, wherein the slit forming the cam-like structure comprises a slit forming a nested cam-like structure.

20. A sensor assembly, comprising:
a flexible and stretchable substrate multi-layer structure, wherein the surface of each layer of the flexible and stretchable substrate multi-layer structure is a nested spiral having attached thereto a number of temperature sensors, said nested spiral formed by one or more slits such that the substrate layer structure stretches to become adapted to a geometry of a body surface under the substrate layer structure, and wherein the layers of the multi-layer structure are separated by a first thermally insulating, stretchable and flexible layer, and one of said layers is mounted in a second thermally insulating, stretchable and flexible layer.

21. The sensor assembly according to claim 20, wherein the substrate layer structure is a two layer structure, each layer including the nested spiral and a number of temperature sensors.

22. A substrate layer structure, comprising:
a plurality of sandwiched flexible substrate layers configured to conform to an ellipsoidally shaped surface of a human or animal body or biological species, and the first flexible substrate layer includes a pattern of one or more slits of a pre-fixed geometry which stretches to expand the first flexible substrate layer in at least two dimensions to conform to the ellipsoidally shaped surface;
a plurality of sensors attached to the flexible substrate layers; and wherein the one or more slits includes cuts which expand the first flexible substrate layer in the at least two dimensions to conform to the ellipsoidally shaped surface.

* * * * *